US009945000B2

United States Patent
Jemaa et al.

(10) Patent No.: US 9,945,000 B2
(45) Date of Patent: Apr. 17, 2018

(54) METHOD FOR RECOVERING AN ACID FROM ACID/SUGAR SOLUTIONS

(71) Applicant: FPINNOVATIONS, Pointe-Claire (CA)

(72) Inventors: Naceur Jemaa, Pointe-Claire (CA); Michael Paleologou, Beaconsfield (CA); Talat Mahmood, Kirkland (CA)

(73) Assignee: FPINNOVATIONS, St-Jean, Pointe-Claire, QC (CA)

( * ) Notice: Subject to any disclaimer, the term of this patent is extended or adjusted under 35 U.S.C. 154(b) by 0 days.

(21) Appl. No.: 15/133,529

(22) Filed: Apr. 20, 2016

(65) Prior Publication Data
US 2016/0312317 A1    Oct. 27, 2016

Related U.S. Application Data

(60) Provisional application No. 62/150,401, filed on Apr. 21, 2015.

(51) Int. Cl.
*C13B 20/00*    (2011.01)
*C13B 20/14*    (2011.01)
(Continued)

(52) U.S. Cl.
CPC ............. *C13B 20/146* (2013.01); *B01J 41/04* (2013.01); *B01J 41/13* (2017.01); *C01B 17/905* (2013.01);
(Continued)

(58) Field of Classification Search
CPC .................................................. C13B 20/146
See application file for complete search history.

(56) References Cited

U.S. PATENT DOCUMENTS

| 3,078,140 A * | 2/1963 | Hatch ..................... B01J 39/19 |
| | | 127/55 |
| 4,608,245 A * | 8/1986 | Gaddy .................. C01B 17/925 |
| | | 127/37 |

(Continued)

FOREIGN PATENT DOCUMENTS

| CA | 2299257 | 2/1999 |
| CA | 2661531 | 2/2008 |

OTHER PUBLICATIONS

Dejak et al, Environmental II Session F Acid Purification and Recovery Using Resin Sorption Technology—A Review, Jan. 2014.*

(Continued)

*Primary Examiner* — Melvin C. Mayes
*Assistant Examiner* — Stefanie J Cohen
(74) *Attorney, Agent, or Firm* — Norton Rose Fulbright Canada LLP

(57) ABSTRACT

Acid hydrolysis of biomass is an important step for releasing the component sugars before converting them to fuels and/or biochemicals. During such a process, a significant amount of mineral acid, such as sulfuric acid, is used. In most cases, the residual acid is neutralized with lime before the sugar conversion step. By doing so, a waste calcium sulphate stream is generated and sent to disposal. The efficient separation of acid from the sugars would allow the recycle of the acid and make the entire process more economically viable. We found that a resin bed packed with an acid retardation resin can be used to achieve an efficient separation (i.e. 98.5% recovery of the acid) of the sulfuric acid from the sugars. The resin bed can be simply regenerated with water.

12 Claims, 2 Drawing Sheets

Figure 1:
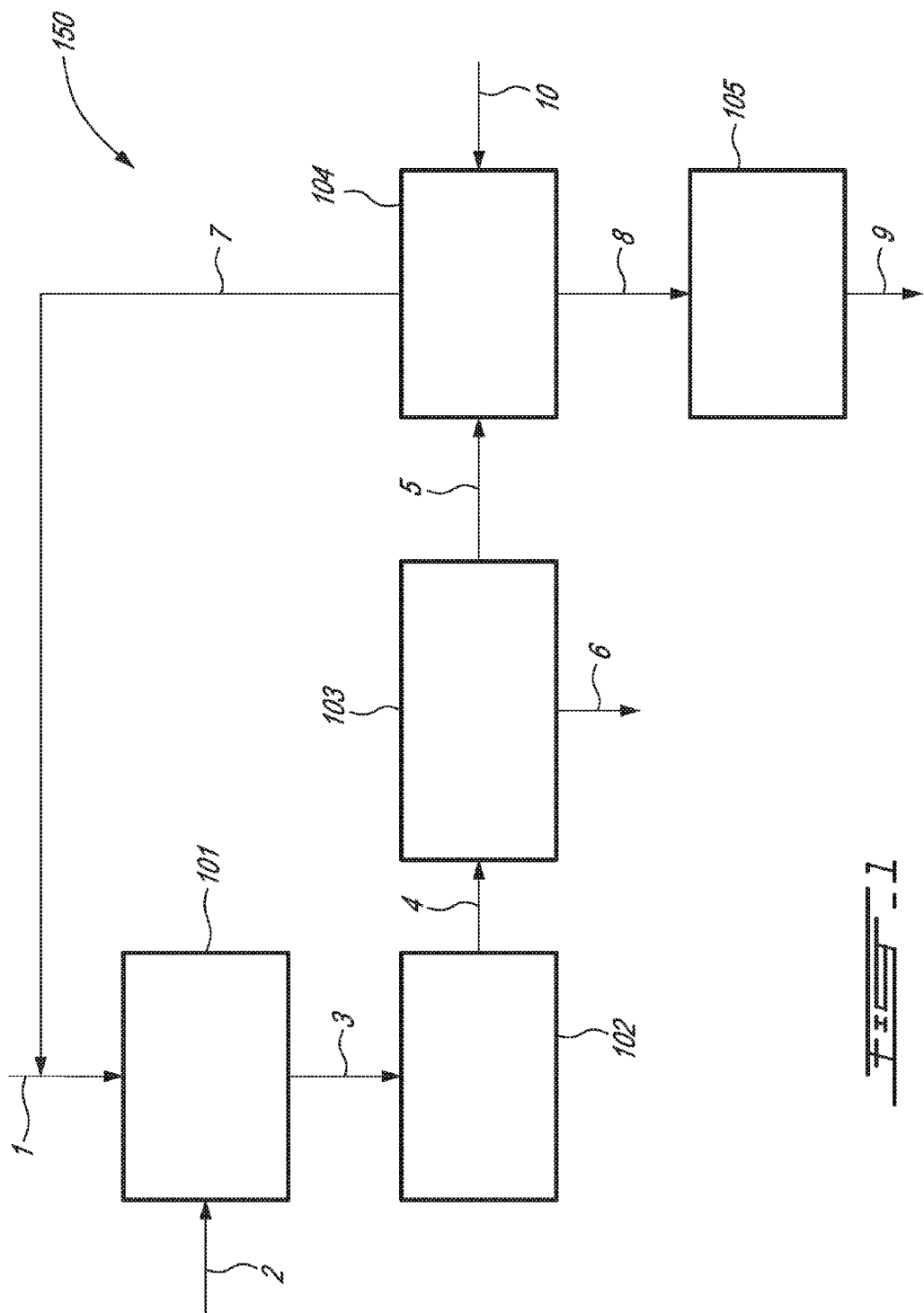

(51) Int. Cl.
  *C07C 51/47*  (2006.01)
  *C01B 17/90*  (2006.01)
  *B01J 41/04*  (2017.01)
  *C13K 1/02*  (2006.01)
  *C13K 13/00*  (2006.01)
  *B01J 41/13*  (2017.01)

(52) U.S. Cl.
  CPC ............... *C07C 51/47* (2013.01); *C13K 1/02* (2013.01); *C13K 13/002* (2013.01)

(56) References Cited

U.S. PATENT DOCUMENTS

| | | |
|---|---|---|
| 4,673,507 A * | 6/1987 | Brown .................. B01J 47/02 210/289 |
| 5,084,104 A | 1/1992 | Heikkila et al. |
| 5,403,604 A | 4/1995 | Black, Jr. et al. |
| 5,407,580 A | 4/1995 | Hester et al. |
| 5,538,637 A | 7/1996 | Hester et al. |
| 5,580,389 A | 12/1996 | Farone et al. |
| 5,628,907 A | 5/1997 | Hester et al. |
| 5,792,441 A | 8/1998 | Paleologou et al. |
| 5,968,362 A | 10/1999 | Russo, Jr. |
| 6,391,204 B1 * | 5/2002 | Russo, Jr. ............ B01D 15/185 127/37 |
| 7,077,953 B2 | 7/2006 | Ranney |
| 7,338,561 B2 | 3/2008 | Theoleyre |
| 2008/0093302 A1 * | 4/2008 | Kearney ............. B01D 15/185 210/656 |

OTHER PUBLICATIONS

Hatch, M. J. and Dillon, Acid Retardation, J. A., Industrial and Engineering Chemistry Process Design and Development 2(4), p. 253-263, Oct. 1963.

Bio-Rad Laboratories, Analytical Grade AG 11 A8 Ion Retardation Resin, Instruction Manual, Catalog No. 732-2032, p. 1-18.

International Search Report dated Jun. 20, 2016 from corresponding PCT/CA2016/050449.

* cited by examiner

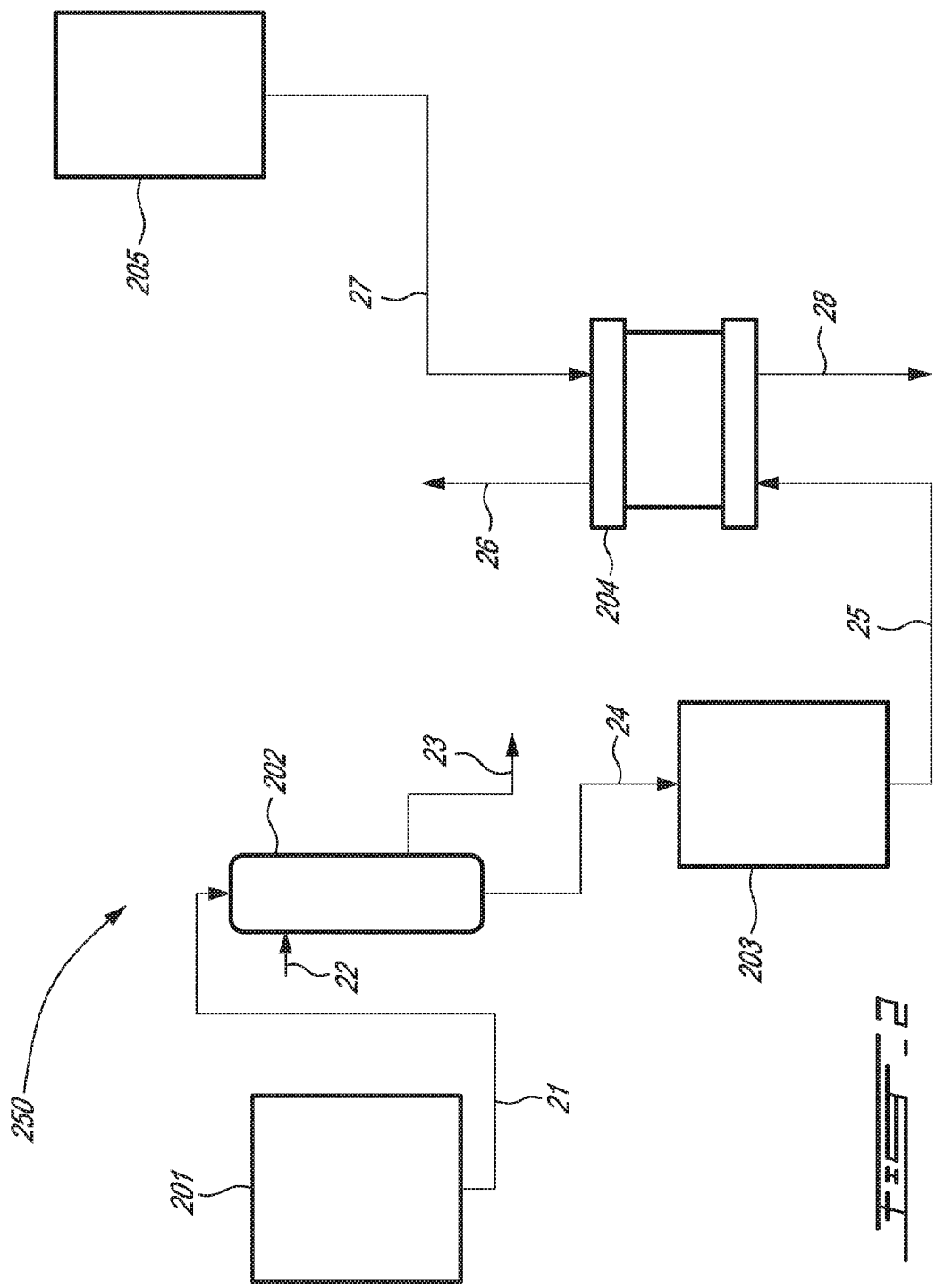

METHOD FOR RECOVERING AN ACID FROM ACID/SUGAR SOLUTIONS

BACKGROUND i) Field

The present relates to the removal and recovery of an acid from a mixture of soluble non-ionic organic compounds and acid. A non-ionic organic compound/acid stream can be generated after biomass hydrolysis with acids or the production of organic acids (e.g. lactic acid, succinic acid, acetic acid) from sugars using fermentation or other means. In particular, the process described herein may be employed to remove the acid from an acid/sugar stream obtained after pulp hydrolysis with sulphuric acid or other acids to produce nanocrystalline cellulose (NCC). This approach enables the recycle of the acid to the hydrolysis step and avoids the use of chemicals to neutralize the stream and the generation of wastes. The de-acidified sugars can be fermented or converted to valuable fuels or chemicals.

ii) Description of the Prior Art

The annual biomass growth on the earth is estimated to be 118 billion tons. The production of fuels and biochemicals from biomass feedstocks is attractive and sustainable. During such processes, the lignocellulosic material is hydrolyzed to break down the polysaccharide components (e.g. cellulose and hemicellulose) into monomeric and oligomeric sugars before converting them to valuable products. This hydrolysis step involves generally the use of a significant amount of mineral acid. Sulfuric acid is generally the acid of choice due to its availability and cost. Different acid concentrations ranging from less than 0.5% to 80% are used to release the sugars. The acid plays the role of a catalyst and is not consumed during the hydrolysis step. After the hydrolysis step, the acid is generally neutralized with lime before sugar fermentation. As a result, significant amounts of calcium sulfate can be generated which need to be dealt with. This practice increases the operating costs associated with the production of sugars and, by extension, sugar-derived biofuels and chemicals. To make the hydrolysis step more economically attractive, the spent acid should be separated and recycled to the process. The recovery and recycle of acid will reduce the cost of the sugar conversion and the cost of waste disposal.

The separation of electrolytes from nonelectrolytes in different applications has been investigated in the prior art. Several approaches such as chromatographic techniques, nanofiltration, reverse osmosis, and crystallization have been suggested and investigated. Chromatographic techniques include ion exchange, ion exclusion and ion retardation. In ion exchange systems, ions (cations or anions) are exchanged between the solute and a resin. Nonelectrolytes in solution have no interaction with the resin and pass straight through the resin bed. Thus, they can be separated from electrolytes using this technique. Several applications of this approach have been devised. Regeneration of the resin is generally performed using chemicals.

In ion exclusion, there is no exchange of ions between the solute and the resin. This technique is used to separate ionic from nonionic (or weakly ionic) species. This technology employs a microporous resin which can sorb water and nonionic solutes. Electrolytes such as sulfuric acid are prevented from entering the porous resin structure due to ion repulsion. Therefore, an electrolyte will pass faster than a nonelectrolyte through a column packed with such a resin. Thus, in ion exclusion it is expected that the acid is eluted first from the resin bed while the sugar exits second because it penetrates deeper in the porous resin. Ion exclusion has been used mainly in analytical and pharmaceutical applications since it is limited to low flows and low concentrations of species.

U.S. Pat. No. 5,403,604 dealt with sugar separation from juices using a set of membrane units including ultrafiltration, nanofiltration (NF) and reverse osmosis. The sugars were retained by the NF membrane while acids such as citric acid passed through. The total acid concentration in the feed stream was about 0.79 wt % while the total sugar varied from 4.3 to 14.3%.

U.S. Pat. No. 7,077,953 dealt with acid recovery from a hydrolysate solution obtained after exposing wood chips to an acidic solution. In this case, the sugars and the acid were contaminated with several other compounds such as lignin, metals, and suspended solids. The inventor used a chromatographic unit to retain and separate most of the sugars from the hydrolysis process. Water was employed to elute the sugars from the chromatographic unit. The eluted sugars were sent to a processing unit such as a fermentation/distillation unit. The chromatographic unit yielded a dilute sugar stream which upon fermentation yielded a diluted product that will require more energy to concentrate. The acid-rich stream from the chromatographic system was processed using a nanofiltration unit to remove the remaining sugars. The inventor also suggested having a second nanofiltration unit ahead of the chromatographic unit to concentrate the sugars. This approach involves the use of several steps which may not be economically viable.

U.S. Pat. No. 5,580,389 discussed the separation of acid from sugars from strong acid hydrolysis of biomass. The method involves several steps such as removal of silica, de-crystallization, hydrolysis, and sugar/acid separation. The latter separation was performed using a cross linked polystyrene cation exchange resin to retain the sugars. The resin was cross-linked with 6 to 8% divinylbenzene and treated with sulfuric acid to produce a strong acid resin. The resin was then washed with water to release the sugars. The sugar solution could thus be fermented to produce value added-products.

U.S. Pat. No. 7,338,561 describes a process for purifying an aqueous solution containing one or several sugars contaminated with multivalent cations, monovalent metal cations, monovalent anions and multivalent inorganic anions and/or organic acid anions. The process employs several separation units including: a strong anionic resin, a strong cationic resin, a nanofiltration device, a crystallization unit, a reverse osmosis unit, and up to two chromatographic columns. This approach was applied to a permeate from an ultrafiltration unit treating whey. Chemicals are needed to regenerate the columns filled with the anionic and cationic resins. The use of all of these units to perform the desired separation is complicated and does not seem to be economically attractive. Also, it is indicative of a low separation efficiency.

Hatch, M. J. and Dillon, J. A., Industrial and Engineering Chemistry Process Design and Development 2(4), 253, October 1963 used an acid retardation resin to separate acids from salts. A similar acid retardation resin has been employed, for example, to purify the waste generator acid (U.S. Pat. No. 5,792,441) produced at kraft pulp mills.

U.S. Pat. No. 5,968,362 describes a method for separating acid and sugars from a biomass acid hydrolysis step. The process employed an anionic exchange resin or an ion-exclusion chromatographic material in a simulated moving bed (e.g. from Advanced Separation Technologies) to retain the acid from the hydrolysate. The sugars produced were contaminated with acid and metals. The author proposed a treatment with lime to neutralize the solution and precipitate the metals.

U.S. Pat. No. 5,628,907 describes the separation of acid-sugar mixtures using ion exclusion chromatography. The separation of glucose from sulfuric acid at different feed concentrations and different modes of operations was reported. Several resins with different degree of divinylbenzene (DVB) cross-linking were employed.

There is still a need for an acid/sugar separation method that is simple and efficient. The method should be more economically viable compared to the other approaches mentioned above which employ several separation steps thereby having high capital and operating costs. Such a method will preferably minimise the dilution of the sugar and acid product streams.

SUMMARY

It is an object to recover and reuse the acid content in a soluble non-ionic organic compound/acid mixture which is in most cases neutralised by lime, for example, and then sent to sewer or landfill.

It is an object to provide a process for separating sulfuric acid from an acid/sugar stream obtained after pulp hydrolysis for the production of nanocrystalline cellulose (NCC).

In accordance with one aspect described herein, there is provided a method for treating a biomass hydrolysate solution containing an acid and non-ionic organic compounds, the method comprising: feeding the hydrolysate solution to a fixed-resin bed of an acid retardation unit, the acid retardation unit comprising a base and a top opposite the base, and the fixed-resin incorporating a particulate quaternary ammonium resin retaining the acid and rejecting the non-ionic organic compound; and eluting the acid retained on the fixed-resin with water to recover a purified acid, wherein more than 90% by weight of the acid in the biomass hydrolysate is recovered.

In accordance with another aspect, there is provided the method herein described wherein more than 75% by weight of the non-ionic organic compound in the biomass hydrolysate is recovered.

In accordance with another aspect, there is provided the method herein described wherein the hydrolysate is fed into a base of the acid retardation unit up through the fixed-resin bed.

In accordance with another aspect, there is provided the method herein described wherein the water eluting the acid is into the top of the acid retardation unit down through the fixed-resin bed.

In accordance with another aspect, there is provided the method herein described wherein the acid is at least one of sulfuric acid, phosphoric acid, nitric acid, hydrochloric acid, formic acid, lactic acid and succinic acid.

In accordance with another aspect, there is provided the method herein described wherein the acid is sulfuric acid from 1 to 98% $H_2SO_4$.

In accordance with another aspect, there is provided the method herein described wherein the non-ionic organic compound is at least one of a soluble sugar and soluble alcohol.

In accordance with another aspect, there is provided the method herein described wherein the non-ionic organic compound is a sugar.

In accordance with another aspect, there is provided the method herein described wherein the particulate quaternary ammonium resin is under compression within the fixed-resin bed.

In accordance with this description, there is provided a method for the separation of sulfuric acid from a solution containing sugars and sulfuric acid comprising the following steps:
a) Removing any suspended solids that might be present in the acid/sugar mixture using filtration.
b) Feeding the acid/sugar solution to a fixed resin bed acid retardation unit containing a particulate quaternary ammonium resin wherein the acid is absorbed by the resin. The de-acidified sugars simply exit the bed and are recovered for further processing.
c) Regenerating the acid retardation unit with water to recover the sulfuric acid solution and reuse it in the hydrolysis step.

DETAILED DESCRIPTION OF THE DRAWINGS

FIG. 1 presents a simplified flow diagram of a biomass hydrolysis process with acid recovery and reuse according to one embodiment described herein; where the acid is separated from a soluble non-ionic organic compound, such as a sugar, using an acid retardation resin and water is used to regenerate the resin bed with the sugar-rich stream further processed to produce biofuels or biochemicals; and FIG. 2 presents a detailed flow diagram of the proposed acid retardation unit (ARU) for acid and sugar separation according to another embodiment described herein.

DETAILED DESCRIPTION

As described above, several approaches were previously proposed for acid/sugar separation. However, in the prior art, no attempt was made to use an ARU to separate the acid from the sugars. In particular, no mention was made of using an ARU to produce a de-acidified sugar stream after pulp hydrolysis of a biomass hydrolysate, and particularly a hydrolysate from the production of nanocrystalline cellulose (NCC).

A hydrolysate solution is defined herein as a solution obtained through hydrolysis, particularly acid hydrolysis, and comprises an acid and non-ionic organic compounds.

The non-ionic compound is understood to be a sugar. Acids are understood to be sulfuric acid, lactic, succinic acetic acid and the like.

An acid retardation resin is a resin with a unique structure that preferentially absorbs strong acids or slows down their movement (retardation) relative to the movement of other chemical compounds (e.g. non-electrolytes). This is different from other chromatographic methods such as ion exclusion chromatography that is known to separate ionic and non-ionic species using a resin as a stationary phase. During this process, the non-ionic substance is sorbed on the resin while the ionic species pass through the bed. As mentioned before, this approach is limited to low flows and low concentrations of species. In the present method ARU, a strong base anion exchange resin (containing quaternary ammonium groups) was found to be capable of absorbing acids while excluding sugars.

The acid retardation process described herein, for the first time recovers acid and (non-ionic) sugars from one another in a reversible manner such that regeneration of the resin is possible using simply water which reduces the operating cost of the separation. In conventional ion exchange technology large resin beds are used which lead to long cycle times (i.e. hours). These long cycles expose the resin to chemicals for extended periods of times and can lead to rapid resin degradation. A commercially available Recoflo® Technology (Eco-Tec Inc., Pickering, Ontario, Canada) characterized by having fast flows and a short cycle time (2 to 5 minutes for all the steps), a short resin bed (from 7.5 to 60 cm in height), fine particle size resins, and frequent resin wash steps was employed herein. The acid retardation resin in a preferred embodiment is kept inside the resin bed under compression or in the so-called "overpacked" condition. The present method uses a simple approach for the separation of soluble non-ionic organic compounds, such as sugars from an acid. This new method is expected to be more economically viable compared to the other approaches mentioned above which employ several separation steps thereby requiring high capital and operating costs. An additional advantage of combining the Recoflo Technology with acid retardation resins is that the dilution of the two product streams is minimised.

Biomass hydrolysis for the conversion of the polysaccharide components (e.g. cellulose and hemicellulose) can be performed using several treatments. Acid hydrolysis of lignocellulosic biomass can be achieved using dilute or concentrated acid. A biomass hydrolysate is defined here as any hydrolysis product of biomass that can derive from but is not limited to wood chips, pulp, bark, sawdust and hog fuel. The acid may be at least one of sulfuric acid, phosphoric acid, nitric acid and hydrochloric acid. Sulfuric acid is generally the acid of choice, which can go from dilute to concentrated acid, or 1 to 98% $H_2SO_4$. Furthermore, the process may separate other soluble non-ionic organic compounds from the acid, these compounds include but are not limited to at least one of a soluble sugar and alcohol. The sugars may be $C_5/C_6$ monomers or oligomers of $C_5/C_6$, while the alcohols are generally $C_{1-10}$. The separated $C_5/C_6$ sugars can be fermented to produce organic acids (e.g. lactic acid, succinic acid) from $C_6$ sugars. The produced organic acids can be separated from the remaining $C_5$ sugars using the ARU described herein. During the hydrolysis step, the acid, at a given concentration, is allowed to react with the biomass at a given temperature and pressure. Sugars are then released into the acidic solution. Lignin present in the biomass has limited solubility and can thus be separated relatively easily from the solution. The remaining solution is basically a mixture of acid and sugar.

The NCC production process involves the grinding of bleached pulp to particles less than 1 mm in size. Concentrated sulphuric acid is then added to the cellulose particles at 45-70° C. The system is left to react, with mechanical stirring, for about 25 minutes. A significant amount of water is then added to dilute the acid and stop the reaction. During a filtration step, the NCC is concentrated and separated from the acid and sugars. The spent liquor/acid solution from this step contains mainly sulphuric acid, sugars and other soluble non-ionic species.

FIG. 1 provides a simplified diagram of a biomass conversion process 150 to useful by-products. Biomass 2 used in the process 150 includes but is not limited to wood chips, pulp, bark, sawdust and hog fuel. The first step is an acid hydrolysis step 101 which takes place in a reactor at a given temperature and pressure. Acid 1, such as sulfuric acid, at a given concentration is introduced with the biomass 2 to an acid vessel. At the end of hydrolysis 101, a mixture of sugar/acid 3 is obtained and is directed to another vessel for settling 102. The liquid portion 4 of the sugar/acid mixture 3 is fed to a separation unit such as a filter 103 to remove any suspended solids 6 from the acid/sugar liquid portion 4. The suspended solids-free solution 5 is fed to an ion-exchange unit specifically an acid retardation resin bed 104. Acid retardation resins are able to pick up both the anion and cation of acids at the same time. Therefore, in this case, the whole acid $H_2SO_4$ molecule is picked-up by the resin. In a preferred embodiment, the resin is placed in a fixed-resin bed of an acid retardation unit with the fixed-resin bed incorporating granular resin particles with quaternary ammonium moieties. In a preferred embodiment the granular resin particles have a constant average particle size of about 50 µm, and maintain their volume during the hydrolysate feeding and acid elution steps, that is, the acid retardation resin does not shrink and expand as much as other chromatographic resins have been known to do.

Any sugar present in solution, having no ionic charge does not significantly interact with and is rejected by the resin thus passing directly through the resin. The sugar stream 8 from the resin bed is directed to the sugar conversion unit 105 for further processing. The sugar conversion unit may consist of several steps to reach the desired biofuel or biochemical product 9 specifications.

To regenerate the resin, water 10 is used to elute the resin bed. During this elution step, the acid 7 is released and exits the bed. The acid can be recycled to the hydrolysis step without any further processing or it can be mixed with fresh concentrated acid to reach the desired concentration of acid used in the hydrolysis step 101. Alternatively, it can be concentrated by evaporation before it is recycled to the hydrolysis vessel step 101. By alternately feeding the sugar/acid solution to the resin bed and eluting the acid from the resin bed with water sugars are separated from the acid.

FIG. 2 shows a more detailed schematic of the ARU system 250. The acid/sugar solution is placed in the feed tank 201. The acid/sugar mixture 21 is fed to a multimedia or other filter 202 to remove any suspended solids that might be present. The filter is periodically washed with water 22. The waste water stream 23 containing the suspended solids and after neutralization is discarded to sewer. The filtered sugar/acid solution 24 is then sent to a feed tank 203 where the solution is heated or cooled down depending on the original temperature of the mixture. The solution 25 is passed through a fixed-resin bed ARU 204 from the bottom. The sulfuric acid is absorbed by the acid retardation resin within the ARU and an acid-lean, sugar-rich solution 26 is obtained from the top of the fixed bed. In a subsequent step, water 27 from the water supply tank 205 is fed to the top of the ARU and down through the fixed-resin bed to regenerate the resin and produce a purified sulfuric acid stream 28 which can be used during the initial hydrolysis process to depolymerise the polysaccharides into simpler sugars.

EXAMPLE 1

During the production of nanocrystalline cellulose (NCC), pulp is hydrolysed with concentrated sulfuric acid at about 45-70° C. followed by several steps to produce purified NCC with the desired properties. During the purification of the NCC particles, a residual solution rich in sulphuric acid and sugars is obtained. This spent acid stream contains mainly sugar oligomers, sugar monomers and acid. The acid cannot be reused because of the presence of sugars. Concentrating the acid using evaporation is expected to lead to the degradation of the sugars by dehydration leading to the formation of products like furfural and hydroxymethyfurfural, other low molecular weight organics as well as carbon deposits on the evaporator tube surface. The efficient separation of the sugars would allow the recycle of the acid. This would also allow the conversion of sugars to other valuable products.

This trial was conducted using a commercially available ARU known as the Acid Purification Unit, APU, (Eco-Tec, Inc., Pickering, Ontario, Canada). The pilot system was equipped with a 20-cm diameter×60 cm height fixed-resin-bed. Table 1 presents the feed composition of a sugar/$H_2SO_4$ mixture from an NCC plant. As shown in this Table, in this experiment, the acid concentration was 150 g/L while the sugar concentration was 117 g/L. After passing the aqueous solution through an ARU system, the sugar-rich stream contained 1.6 g/L $H_2SO_4$ and 81.2 g/L sugar. The acid-rich stream contained 82 g/L $H_2SO_4$ and 17.7 g/L sugar. In this case, more than 98.5% of the sulfuric acid was recovered.

TABLE 1

Acid/sugar separation using an acid retardation resin

| | Flow rate, L/hr | Acid, g/L | Sugar, g/L |
|---|---|---|---|
| Feed solution | 131 | 150 | 117 |
| Sugar-rich stream | 142 | 1.6 | 81.2 |
| Acid-rich stream | 236 | 82 | 17.7 |

After separation, the sugar-rich stream was sent to an anaerobic treatment plant for biogas production. The stream was first neutralized with sodium hydroxide. Removing the acid from the original acid/sugar mixture led to less caustic usage and a considerable reduction in the solution ionic strength. A high solution ionic strength is known to reduce the growth of microorganisms thereby negatively affecting the biogas production. The amount of biogas produced from the de-acidified sugar was about 0.51 L/kg of sugar. The biogas contained about 67% methane. The sulfate content of the sugar-rich stream was too low to be a problem during biogas production in terms of hydrogen sulphide generation.

EXAMPLE 2

This test was conducted using a commercially available ARU known as the APU (Eco-Tec, Inc., Pickering, Ontario, Canada). The pilot system was equipped with a 5-cm diameter×60 cm height fixed-resin-bed. Data generated from such a system are reliable to predict the operation of full-scale units. Table 2 presents the feed composition of another sugar/$H_2SO_4$ mixture generated during the production of NCC under different conditions from those of Example 1. In the feed solution, the acid and the sugar concentrations were lower compared to the previous case at 73 g/L and 7.2 g/L, respectively. In this case, different operating conditions were employed including a smaller resin bed. After passing the aqueous solution through an ARU system, the sugar-rich stream contained 1.0 g/L $H_2SO_4$ and 4.0 g/L sugar. The acid-rich stream contained 49 g/L $H_2SO_4$ and 1.5 g/L sugar. The sulfuric acid recovery remained high at about 91.6%.

TABLE 2

Acid/sugar separation using an acid retardation resin

| | Flow rate, L/hr | Acid, g/L | Sugar, g/L |
|---|---|---|---|
| Feed solution | 8.5 | 73 | 7.2 |
| Sugar-rich stream | 11.5 | 1.0 | 4.0 |
| Acid-rich stream | 11.6 | 49 | 1.5 |

The scope of the claims should not be limited to the preferred embodiments set forth in the examples, but should be given the broadest interpretation consistent with the description as a whole.

EXAMPLE 3

The following tests were conducted using a laboratory glass column filed with the same acid retardation resin used in examples 1 and 2 to investigate the affinity of the resin towards organic acids. The column had a diameter of about 25 mm and was filled with resin. The resin occupied a volume of 100 mL. A solution containing an organic acid with xylose was employed. Organic acids such as lactic acid, acetic acid, and succinic acid were used in these trials. After the acid uptake step, the resin was regenerated with water.

A feed solution of succinic acid (14.53 g/L as succinate) and 11.3 g/L of xylose was passed through the resin bed at room temperature. Table 3A shows the uptake and release of succinic acid. After the first two 0.4 bed volumes, the solution exiting the column contained no succinate. All the succinic acid was picked up by the resin. The xylose content in the second 0.4 bed volume was equal to that of the feed solution indicating that the resin has low affinity for xylose. Regeneration using water indicated that succinic acid can be released from the resin bed.

TABLE 3A

Succinic acid removal using an acid retardation resin

| | Bed Volume = 100 ml | Succinate, g/L | Xylose, g/L |
|---|---|---|---|
| Feed | | 14.53 | 11.3 |
| Acid uptake | 0.4 | 0 | 5.16 |
| | 0.4 | 0 | 11.3 |
| Regeneration | 0.5 | 11.99 | — |
| | 0.5 | 11.94 | — |

A feed solution of lactic acid (9.51 g/L as lactate) and 5.12 g/L of xylose was passed through the resin bed at room temperature. Table 3B shows the uptake and release of lactic acid during this test. After the first 0.33 bed volume, the solution exiting the resin bed contained no lactic acid. The second bed volume was not analyzed. After the third 0.33 bed volume, the lactic acid concentration was 9.05 g/L. The xylose contained in the third bed volume was 4.97 g/L indicating that the resin has low affinity for xylose. Regeneration using water indicated that the lactic acid can be released from the resin bed. These results clearly indicate that the resin retains the acid, and releases the acid when regenerated. The sugars do not interact with the resin.

TABLE 3B

Lactic acid removal using an acid retardation resin

| | Bed Volume = 100 ml | Lactate, g/L | Xylose, g/L |
|---|---|---|---|
| Feed | | 9.51 | 5.12 |
| Acid uptake | 0.33 | 0 | 2.02 |
| | 0.33 | — | — |
| | 0.33 | 9.05 | 4.97 |
| Regeneration | 0.39 | 8.98 | — |
| | 0.52 | — | — |
| | 0.42 | 0.46 | — |

A feed solution containing acetic acid (3.5 g/L as acetate) and 28.0 g/L of xylose was passed through the resin bed at room temperature. Table 3C shows the uptake and release of the acetic acid during this test. After the first 0.38 bed volume, the solution exiting the column contained no acetic acid. After the third 0.38 bed volume, the acetic acid concentration was 0.69 g/L. Once again the second bed volume was not analyzed. The xylose content in the third 0.38 bed volume was 27 g/L (compared to 28 g/L in the feed). Regeneration using water indicated that the acetic acid can be released from the resin bed.

TABLE 3C

Acetic acid removal using an acid retardation resin

| | Bed Volume = 100 ml | Acetate, g/L | Xylose, g/L |
|---|---|---|---|
| Feed | | 3.5 | 28.0 |
| Acid uptake | 0.38 | 0 | 11.2 |
| | 0.38 | — | — |
| | 0.38 | 0.69 | 27 |
| Regeneration | 0.38 | 1.78 | — |
| | 0.52 | — | — |
| | 0.42 | 0.14 | — |

As explained before, these examples illustrate that after fermenting $C_6$ sugars to lactic/or succinic acid, the $C_5$ sugars can be separated from the mixture using an acid retardation unit. Thus, the $C_5$ sugars can, subsequently, be used to produce other valuable chemicals such as furfural or xylitol.

The invention claimed is:

1. A method for treating a biomass hydrolysate solution containing an acid and non-ionic organic compound, the method comprising:
   feeding the hydrolysate solution to a fixed-resin bed of an acid retardation unit, the acid retardation unit comprising a base and a top opposite the base, and the fixed-resin incorporating a particulate quaternary ammonium resin retaining the acid and rejecting the non-ionic organic compound; and
   eluting the acid retained in the fixed-resin with water to recover a purified acid,
   wherein more than 90% by weight of the acid in the biomass hydrolysate solution is recovered.

2. The method of claim 1 wherein more than 75% by weight of the non-ionic organic compound in the biomass hydrolysate is recovered.

3. The method of claim 1 wherein the hydrolysate is fed into a base of the acid retardation unit up through the fixed-resin bed.

4. The method claim 1 wherein the water eluting the acid is into the top of the acid retardation unit down through the fixed-resin bed.

5. The method of claim 1 wherein the acid is at least one of sulfuric acid, phosphoric acid, nitric acid, hydrochloric acid, formic acid, lactic acid and succinic acid.

6. The method of claim 5 wherein the acid is sulfuric acid from 1 to 98% H2SO4.

7. The method of claim 1 wherein the non-ionic organic compound is at least one of a soluble sugar and soluble alcohol.

8. The method of claim 1 wherein the non-ionic organic compound is a sugar.

9. The method of claim 1 wherein the particulate quaternary ammonium resin is under compression within the fixed-resin bed.

10. The method of claim 1, wherein the particulate quaternary ammonium resin has a constant average particle size of 50 μm.

11. The method of claim 1, wherein the feeding of the hydrolysate has a duration of 2 to 5 minutes.

12. The method of claim 1, wherein the eluting the acid has a duration of 2 to 5 minutes.

* * * * *